US007726588B2

(12) United States Patent
Wuttke et al.

(10) Patent No.: US 7,726,588 B2
(45) Date of Patent: Jun. 1, 2010

(54) LOCKING-TENSIONING MECHANISM FOR A MINIATURISED HIGH PRESSURISER

(75) Inventors: Gilbert Wuttke, Dortmund (DE); Michael Schyra, Wuppertal (DE); Andreas Fiol, Munich (DE); Joachim Eicher, Dortmund (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 11/174,327

(22) Filed: Jul. 1, 2005

(65) Prior Publication Data

US 2005/0269424 A1 Dec. 8, 2005

Related U.S. Application Data

(62) Division of application No. 10/233,918, filed on Sep. 3, 2002, now Pat. No. 6,945,472.

(60) Provisional application No. 60/332,638, filed on Nov. 6, 2001.

(30) Foreign Application Priority Data

Sep. 4, 2001 (DE) ................................ 101 43 350

(51) Int. Cl.
*B05B 11/02* (2006.01)

(52) U.S. Cl. ......................... 239/321; 239/73; 239/324; 239/589; 604/68; 604/135; 222/43; 222/390

(58) Field of Classification Search ................. 239/320, 239/321, 324, 329, 537, 538, 539, 589, 71, 239/73; 604/68, 70, 71, 72, 131, 134, 135; 222/43, 390; 27/320, 321, 324, 329, 537, 27/538, 539, 589
See application file for complete search history.

(56) References Cited

U.S. PATENT DOCUMENTS

| | | | | | |
|---|---|---|---|---|---|
| 2,605,763 | A | * | 8/1952 | Smoot | 604/70 |
| 4,850,967 | A | * | 7/1989 | Cosmai | 604/68 |
| 5,679,111 | A | * | 10/1997 | Hjertman et al. | 604/135 |
| 5,891,086 | A | * | 4/1999 | Weston | 604/70 |

(Continued)

FOREIGN PATENT DOCUMENTS

WO 82/04409 A1 12/1982

(Continued)

OTHER PUBLICATIONS

International Search Report for PCTIEP2002/09146 mailed Dec. 20, 2002.

*Primary Examiner*—Steven J Ganey
(74) *Attorney, Agent, or Firm*—Michael P. Morris; Mary-Ellen M. Devlin; David L. Kershner

(57) ABSTRACT

A locking tensioning mechanism for a miniaturised high pressure generator is disclosed, which mechanism will allow delivery of a set volume of a liquid, and the volume to be delivered by a high pressure generator can be altered subsequently by adjusting one of the stops of the spring component, which locking tensioning mechanism may be used in a high pressure generator for producing an inhalable aerosol or in a needleless injector for injecting a volume of a liquid into animal or plant tissue.

1 Claim, 10 Drawing Sheets

U.S. PATENT DOCUMENTS

Figure 1B:
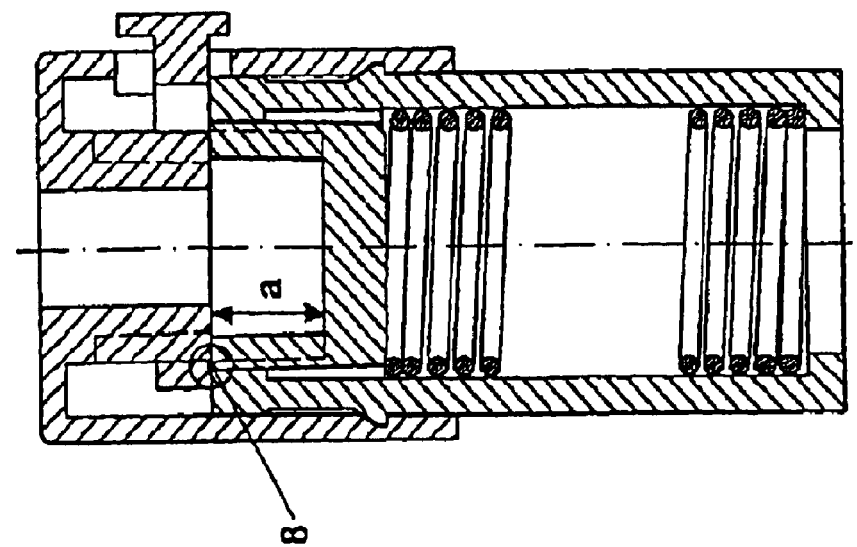

| | | | |
|---|---|---|---|
| 5,899,879 A * | 5/1999 | Umbaugh | 604/68 |
| 5,911,703 A * | 6/1999 | Slate et al. | 604/135 |
| 6,203,521 B1 * | 3/2001 | Menne et al. | 604/68 |
| 6,689,092 B2 * | 2/2004 | Zierenberg et al. | 604/72 |

FOREIGN PATENT DOCUMENTS

| | | | |
|---|---|---|---|
| WO | 95/03844 A1 | 2/1995 | |
| WO | 97/12687 A1 | 4/1997 | |
| WO | 97/20590 A1 | 6/1997 | |
| WO | 97/20596 A1 | 6/1997 | |
| WO | 01/64268 A1 | 9/2001 | |
| WO | 2404360 A1 | 9/2001 | |

\* cited by examiner

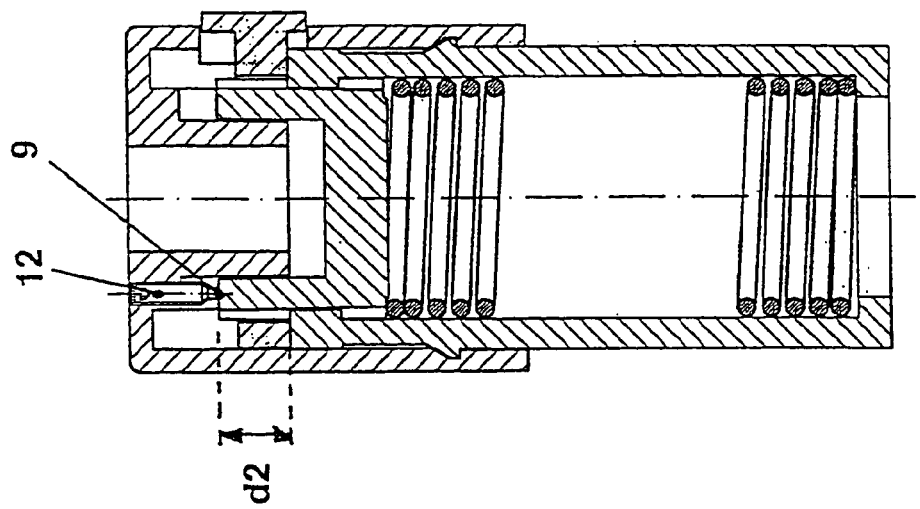
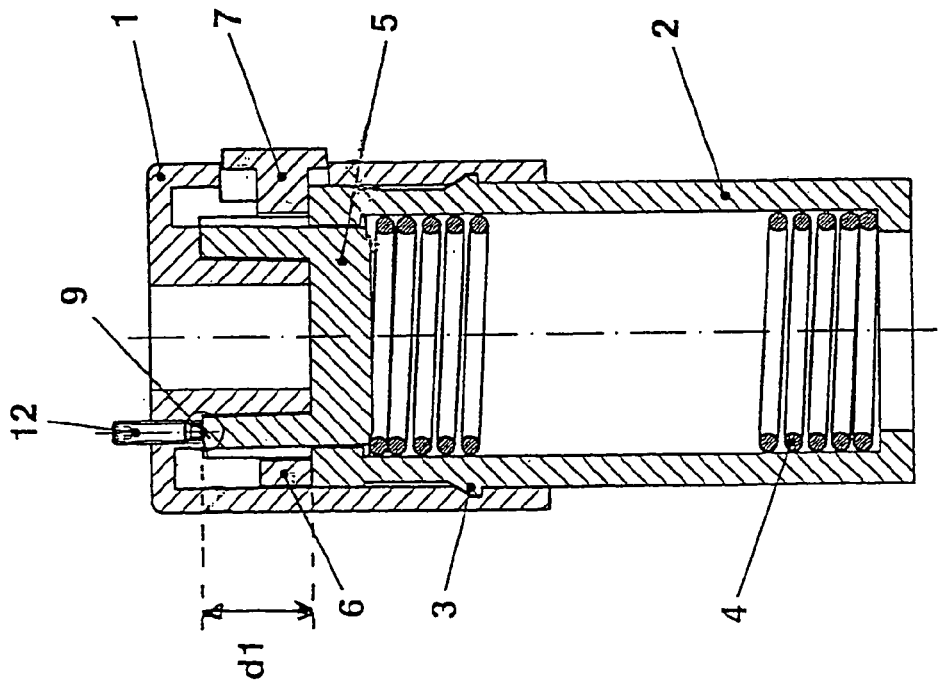
Fig. 4a
Fig. 4b

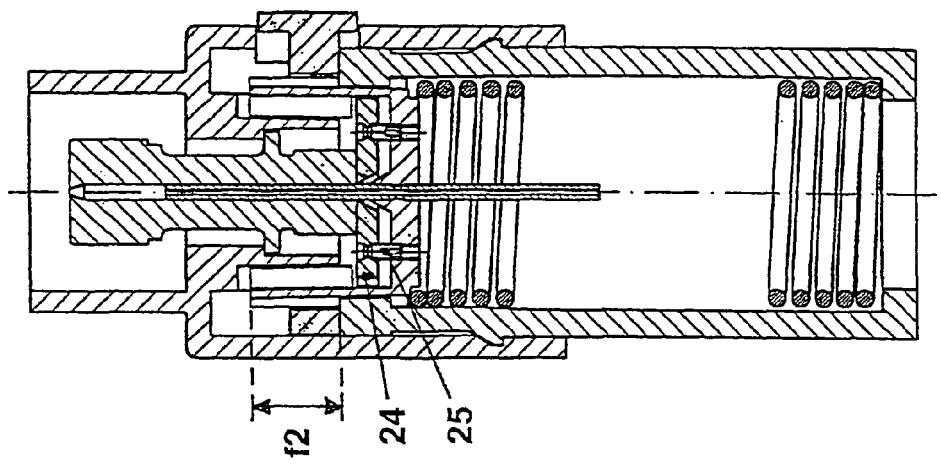
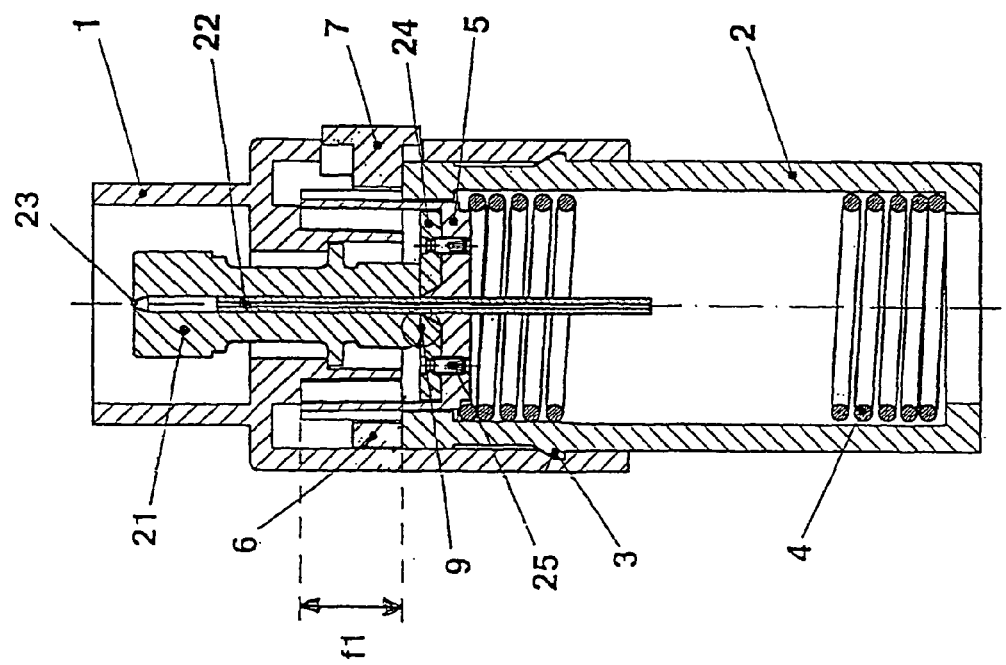
Fig. 6a
Fig. 6b

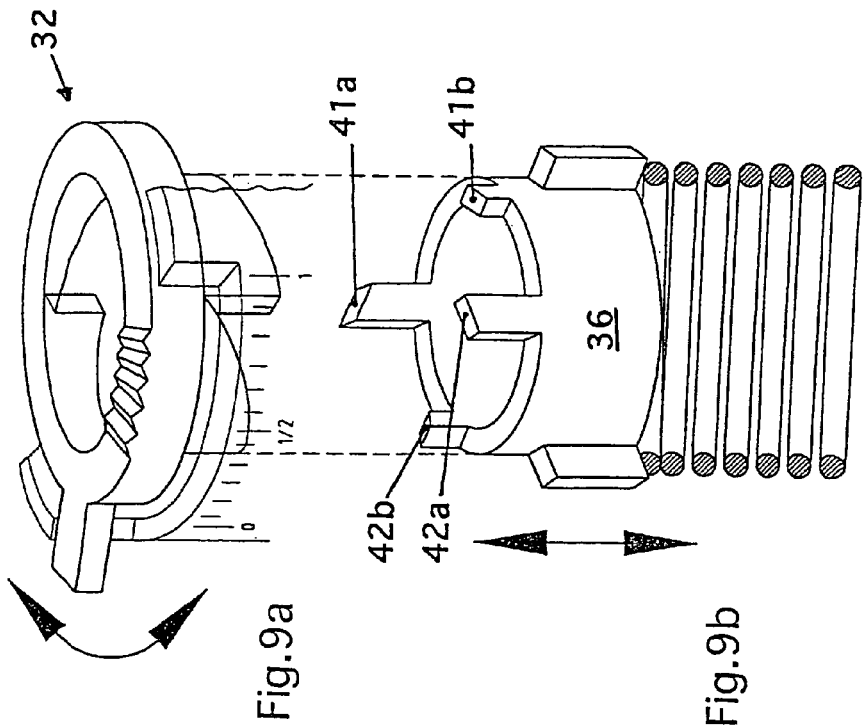
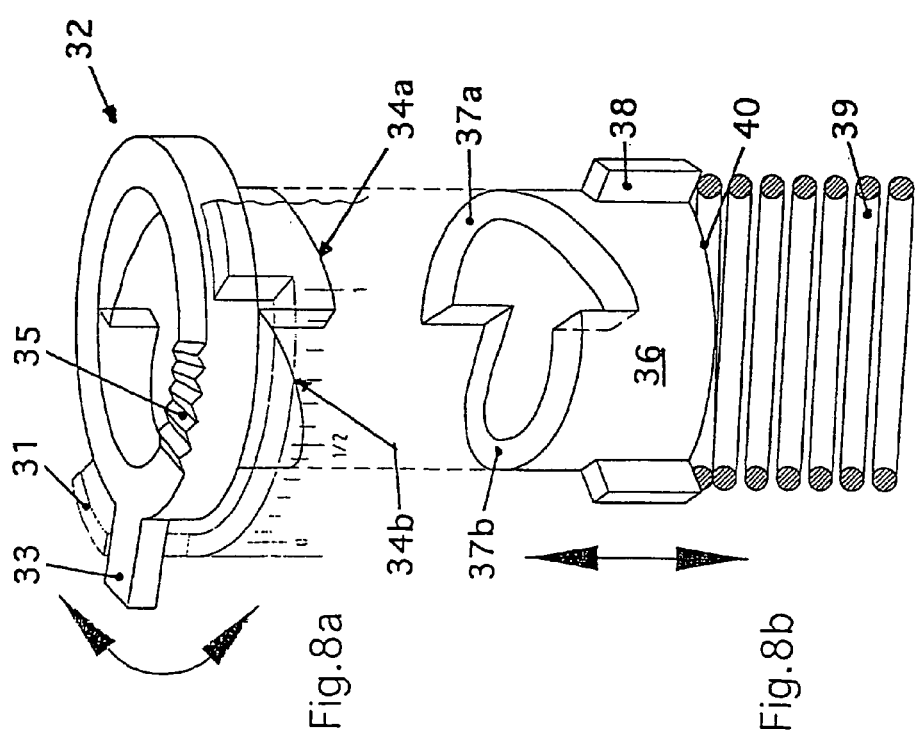

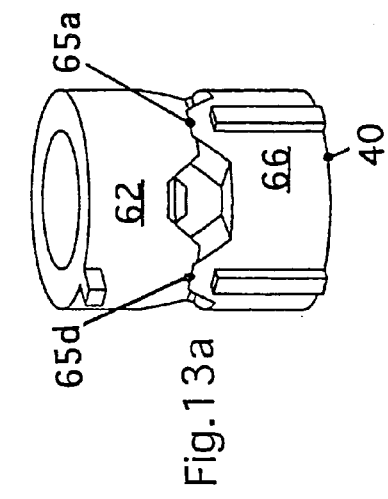
Fig.13a
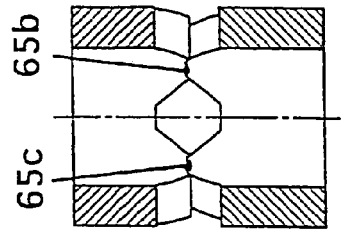
Fig.13b
Fig.13
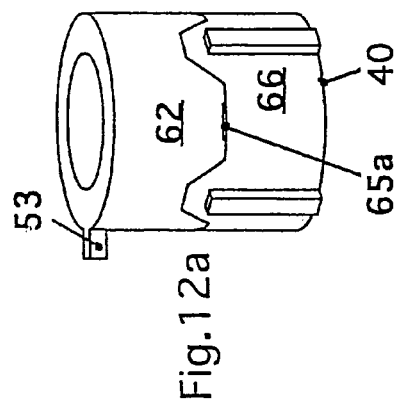
Fig.12a
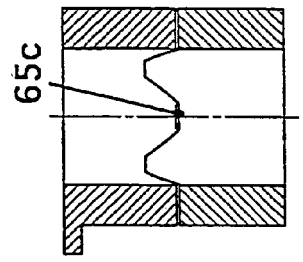
Fig.12b
Fig.12
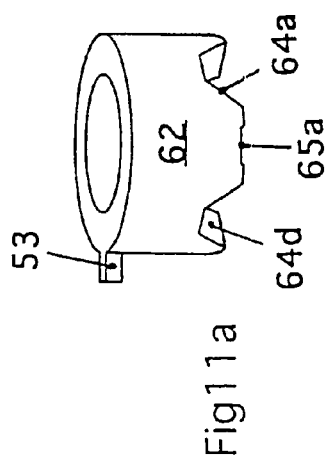
Fig.11a
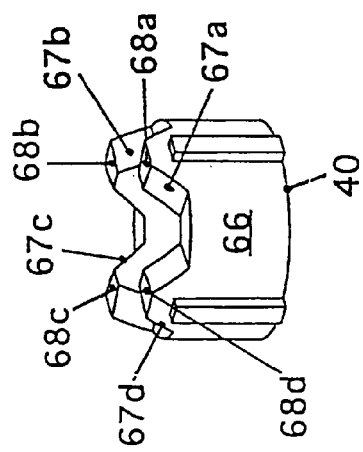
Fig.11b
Fig.11

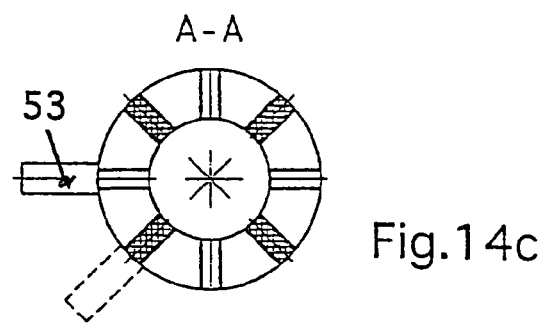
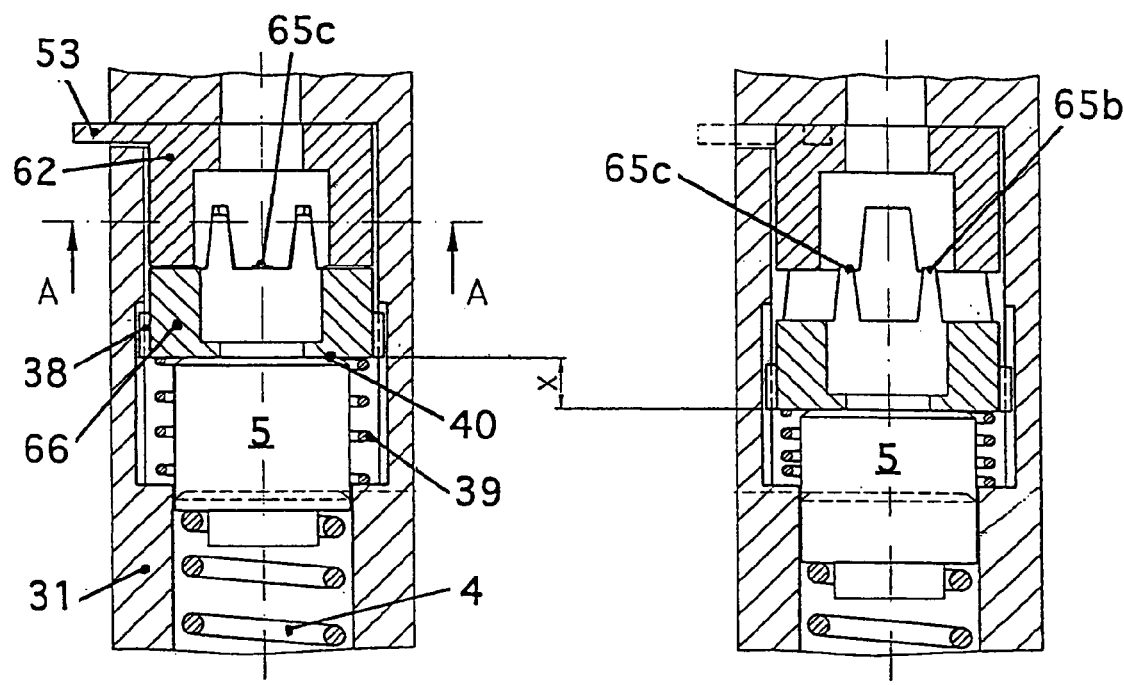
Fig. 14

LOCKING-TENSIONING MECHANISM FOR A MINIATURISED HIGH PRESSURISER

The invention relates to a locking tensioning mechanism for a miniaturised apparatus for applying high pressure to a liquid, wherein the volume of liquid delivered is variable. A high pressure generator of this kind may be used, for example, in an atomiser with which a specified volume of a liquid held under high pressure is atomised to form an aerosol. The high pressure generator may also be used to produce a high pressure jet of liquid of preferably very small diameter.

The liquid may, for example, contain a pharmaceutically active substance. The liquid may be atomised using a high pressure generator to form an aerosol, e.g., a pharmaceutical aerosol which is administered through the lungs or the nasal passages. Using a needleless injector, a liquid medicament can be administered or injected parenterally or the device is used to produce an aerosol mist for application to the eye.

The aim of the invention is to expand the range of uses of a miniaturised high pressure generator of this kind and to adapt the devices to the user's requirements.

In the known locking tensioning mechanisms (W. Krause: Konstruktionselemente der Feinmechanik, Verlag Carl Hanser, München 1993, pages 521 to 523) the energy stored in a spring is released when required and converted into motion. The spring acts on a guided or mounted component, referred to as the spring component. A locking member prevents the spring component from moving and releases it in a predetermined manner.

WO 97/20590 discloses a locking tensioning mechanism for a spring-operated power take-off. This locking tensioning mechanism essentially comprises a power-transmission gear, e.g., a helical thrust gear, for tensioning the spring which applies the power required for the specified high pressure, an annularly arranged locking member with engaging locking surfaces and an actuating button, a spring component and two stops as travel limiters for the spring component. These components are accommodated in a two-part housing; the two parts of the housing are mounted so as to be rotatable relative to one another. In order to tension the spring the two housing parts are rotated relative to one another (e.g., by hand), the helical thrust gear thereby converting the rotary movement of the two housing parts relative to one another into a compression of the spring. At the end of the rotary movement of the two housing parts relative to one another the locking member jumps into its position of engagement and holds the spring component and hence the tensioned spring in this position. If the miniaturised high pressure generator is, e.g., an atomiser according to WO 97/12687, the outlet nozzle producing the aerosol mist is held in front of or inside a body cavity, and the atomising process is initiated by operating the actuating button. If the high pressure generator is a generator of a spray jet, e.g., a needleless injector according to WO 01/64268, the nozzle is pressed against the animal or plant tissue, the needleless injector is actuated by operating the actuating button, and a volume of a liquid is injected into the tissue.

The high pressure generators with the locking tensioning mechanism described in WO 97/20590 reproducibly deliver a given volume of a liquid in the microliter range. The volume delivered is determined by the construction and cannot subsequently be altered. The volume can only be changed by modifying the construction, which is a comparatively expensive process, as the tools for producing the individual components have to be adapted to the altered specification.

The problem of the present invention is to provide a high pressure generator having a locking tensioning mechanism with means for adjusting the volume to be delivered, without altering the essential components of the locking tensioning mechanism or the high pressure generator. The locking tensioning mechanism for the spring-operated power take-off comprises essentially the following components: two housing parts mounted to be movable relative to one another, an operating spring which acts as a store for the mechanical energy acting on a power takeoff flange as the spring component, a device for tensioning the operating spring, a first and a second stop for the spring component which respectively determine the first and second resting positions of the spring component, a piston connected to the spring component which is moved axially in a cylinder as the spring component moves, the piston expelling the volume of liquid as it moves towards an outlet nozzle.

This problem is solved according to the invention by at least one additional component which varies the position of one of the two stops for the spring component and thereby alters the distance travelled by the spring component.

The two housing parts which are movable relative to one another may be mounted so as to be rotatable relative to one another about their axis or axially movable relative to one another. The operating spring may be tensioned by means of a helical thrust gear in the case of housing parts which are mounted so as to be rotatable relative to one another, for example. When the housing parts are mounted to be slidable relative to one another one housing part may be pulled out from the other housing part to a limited extent in order to tension the operating spring. The piston connected to the spring component may be a solid piston or a hollow piston. The spring component may, for example, be disc-shaped or cup-shaped.

The first stop for the spring component forms the travel limiter for the spring component in its first resting position in which the operating spring is tensioned. In this state the locking member is engaged. The second stop for the spring component forms the travel limiter for the spring component in its second resting position, in which the operating spring is relatively relaxed. In this state the locking member is disengaged. By rotating the two housing parts relative to one another the spring component is pushed from its second resting position into its first resting position by means of the helical thrust gear in order to tension the operating spring. After the locking member has been disengaged by operating the actuating button the operating spring pushes the spring component from its first resting position into its second resting position.

The minimum of one additional component by means of which the position of the second stop for the spring component is changed may be, for example:

a spacer disc or a spacer ring of constant thickness,
a pair of stepped discs of variable thickness,
a plurality of pins or screws arranged outside the axis of the device, in the bottom of the cup-shaped spring component or in the housing part which contains the locking member,
a locknut screwed onto the spring component,
an adjustable abutment plate,
a screw mounted centrally with respect to the axis of the device,
a second stop which can be varied over a number of stages, with which the volume to be delivered by the high pressure generator can be divided into a number of portions,
a helical thrust gear for setting a stop of the spring component, the helical thrust gear comprising a rotatable adjusting ring and an axially movable ring, both of which have a helicoidal surface.

The helical thrust gear for setting a stop of the spring component is to be distinguished from the helical thrust gear for tensioning the operating spring mentioned above by way of example.

For example, the second resting position of the spring component can be varied as follows:

A disc or ring of constant thickness is placed on the bottom of the cup-shaped spring component, preferably in the form of a cylinder open at one end. The travel of the spring component is altered by an amount equal to the thickness of the disc or ring. The disc or ring may be clamped or glued in the spring component. The edge of the disc or ring may be smooth or provided with gripping serrations.

The spring component is provided, inside its base, with a plurality of blind holes (e.g., with three holes which are azimuthally offset from each other by 120 degrees). Pins are inserted into the blind holes, from which they protrude. The travel of the spring component is altered by an amount equal to the part of the pins protruding from the blind holes.

Screws are inserted in the blind holes. The travel of the spring component is altered by an amount equal to the part of the screws protruding from the blind holes. The base of the spring component is provided with several (e.g., three) through-holes into which screws projecting into the interior of the spring component are inserted from the side of the spring component facing the spring. The travel of the spring component is altered by an amount equal to the length of the sections of the screws projecting into the interior of the spring.

Screws acting on the second stop for the spring component are screwed into the upper housing part from the nozzle end of the high pressure generator. These screws may be accessible from the outside.

A central screw with a hollow piston secured therein is screwed into the base of the spring component. The part of the central screw projecting into the interior of the cup-shaped spring component alters the travel of the spring component. In this embodiment of the invention the hollow piston is forcibly pushed further into the cylinder by this same amount. The clearance volume in front of the end of the hollow piston facing the outlet nozzle remains virtually unchanged.

The position of one of the two stops of the spring component of the locking tensioning mechanism may also be altered by means of a rotatable adjusting ring which cooperates with an axially movable ring in the manner of a helical thrust gear. The rotatable adjusting ring has a handle projecting from the housing and accessible from outside. The rotatable adjusting ring and the axially movable ring each have a helicoidal surface in which the two rings slide relative to one another. The helicoidal surface may be a right-handed screw or a left-handed screw.

The rotatable adjusting ring is rotatably mounted inside the housing. It may be axially supported against the housing on its side opposite the helicoidal surface axial. The axially movable ring is secured against rotation inside the housing. The side of the movable ring located opposite the helicoidal surface is one of the two stops of the spring component of the locking tensioning mechanisms, either the first or the second stop. The rotatable adjusting ring may be positioned as desired within a given angular range in both directions of rotation. The prescribed range of rotation is limited by the actual construction, e.g., to less than 180 degrees, preferably less than 90 degrees.

When the rotatable adjusting ring is rotated, this alters the spacing of the abutment surface of the axially movable ring from the side on which the rotatable adjusting ring is supported against the housing. This reproducibly changes the position of the first or second stop of the spring component of the locking tensioning mechanism and adjusts the permitted travel of the spring component.

The helicoidal surface of the helical thrust gear may be a single-threaded helicoidal surface if the angle of rotation of the rotatable adjusting ring is less than 90 degrees, for example. For reasons of strength and uniform distribution of force within the helical thrust gear it may be advisable to construct the helicoidal surface as a multi-threaded helicoidal surface, for example as a double-, triple- or quadruple-threaded helicoidal surface.

The helicoidal surfaces on the rotatable adjusting ring and on the axially movable ring may be continuous, over an angle of up to 360 degrees in the case of a single-threaded helicoidal surface, up to an angle of 180 degrees in each case, in the case of a double-threaded helicoidal surface, and up to an angle of 90 degrees in each case, in the case of a quadruple-threaded helicoidal surface. In addition, the helicoidal surfaces on one or both rings may be present only partially over a smaller one of these angles.

The thread height of the helicoidal surfaces is equally great in a pair of cooperating rings. The thread height may be selected freely within a range determined by the manufacturing constraints. Within limits imposed by the construction, the distance travelled by the axially movable ring at a given angle of rotation of the rotatable ring can be adjusted by a suitable thread height of the helicoidal surface.

The helical thrust gear may have engaging means—preferably in the form of engaging teeth, for example—which prevent the helical thrust gear from being shifted accidentally. Such a gear can only be shifted if there is a sufficient rotational force acting on the rotatable adjusting ring. The engaging means may be provided on the side of the rotatable adjusting ring on which the adjusting ring rests on the housing. Moreover, the engaging means may be provided on the helicoidal surfaces—preferably for example in the form of engaging teeth or engaging steps.

If the helicoidal surfaces are provided in each case on one edge of each ring, the rotatable adjusting ring can only push the axially movable ring in front of it; the rotatable adjusting ring cannot pull the axially movable ring back. In this embodiment of the helical thrust gear the axially movable ring can be pressed against the adjusting ring by means of a resetting spring.

In another embodiment the helicoidal surfaces may be provided in or on the cylindrical wall of the rings, for example as double-threaded detents in one ring and as double-threaded cams in the other ring. The cams slide in the detents, and the axially movable ring can be pushed in both axial directions as the rotatable adjusting ring is rotated. In this embodiment no resetting spring is required. The cams may for example be shaped as helicoidal surfaces; they may also be shaped as cylinders protruding from the wall.

In another embodiment it is possible to mount one of the helicoidal surfaces not on the axially movable ring but directly on the side of the spring component facing the rotatable adjusting ring, if the axially movable spring component is secured against rotation inside the housing. In this embodiment either the first stop or the second stop of the spring component may be constructed as a helicoidal surface, and consequently the position of the first stop or second stop can be varied.

The locking tensioning mechanism according to the invention has the following advantages:

Depending on the particular embodiment of the invention the volume to be delivered by the high pressure generator can easily be altered during the assembly of the high pressure generator, or before it is used or while it is being used.

The volume of liquid to be delivered may be varied either continuously or stepwise.

The operating range of the operating spring during the expulsion of the volume of liquid begins with the change, according to the invention, in the second resting position of the spring component under high spring tension. The particle size distribution of the aerosol produced by the high pressure generator or the speed which the needleless injector imparts to the volume of liquid expelled remain virtually unchanged by the change in the second stop for the spring component.

When the position of the second stop for the spring component is changed according to the invention, the position of the first stop for the spring component as well as the nature and mode of operation of the locking member are unaffected.

If, in a locking tensioning mechanism for a high pressure atomiser or for a needleless injector, not only is the second stop for the spring component altered, but the position of the (hollow) piston in relation to the spring component is also altered to the same extent, the clearance volume for the liquid located inside the cylinder between the end of the (hollow) piston facing the outlet nozzle and the nozzle body can be kept at a prescribed value.

The invention is preferably used in a high pressure generator according to Patent Application WO 91/14468 or WO 97/12687, i.e. atomisers for producing pharmaceutical aerosols for administration by inhalation or by nasal route, a needleless injector according to WO 01/64268 or an eye spray device according to PCT/EP0207038.

The devices mentioned above are based on the same mechanism for applying high pressures to a given amount of a liquid. For example, this discussion will therefore be directed to the high pressure generator mentioned above. In the event of any differences or inconsistencies in the specific descriptions between the embodiments of the invention mentioned above or illustrated in the Figures, and the embodiments that follow, the embodiments described above and those illustrated in the Figures are preferred over the embodiments that follow.

An apparatus of this kind for propellant-free atomisation of a metered quantity of a liquid pharmaceutical composition is described in detail for example in International Patent Application WO 91/14468 "Atomizing Device and methods" and also in WO 97/12687, in FIGS. 6a and 6b and the associated description. In a nebuliser of this kind a pharmaceutical solution is converted into an aerosol with an average particle size (mean aerodynamic diameter) of less than 20 microns by the application of high pressures up to 500 bar and sprayed. Reference is hereby made to the abovementioned publications in their entirety within the scope of the present specification.

In nebulisers of this kind the formulation solutions are stored in a reservoir. The active substance formulations used must have sufficient stability when stored and at the same time must be such that they can be administered directly, if possible without any further handling, to suit the medicinal purpose. Moreover they should not contain any ingredients that are able to interact with the nebuliser in such a way that the nebuliser or the pharmaceutical quality of the solution, or of the aerosol produced, might be harmed.

Figure 1A:
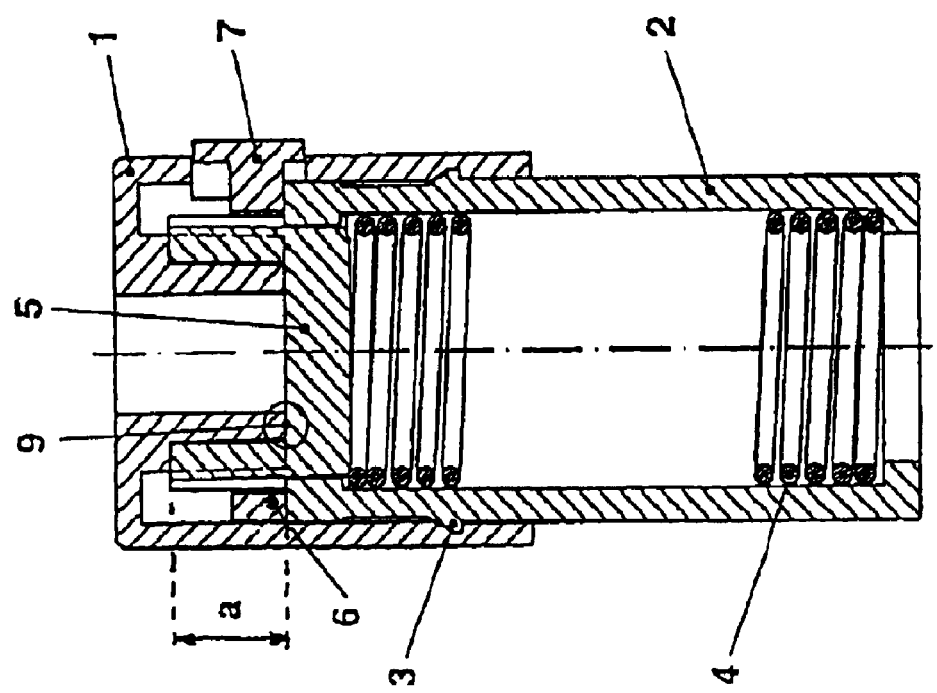

To nebulise the solution a special nozzle is used as described for example in WO 94/07607 or WO 99/16530, particularly FIG. 1 and the associated description. Reference is hereby specifically made to both publications.

The preferred atomiser essentially consists of an upper housing part, a pump housing, a nozzle, an adapter, the locking mechanism according to the invention, a spring housing, a spring and a storage container, the outstanding features of the nebuliser being as follows:

a pump housing which is secured in the upper housing part and which comprises at one end a nozzle body with the nozzle or nozzle arrangement, a hollow piston with valve body, a power takeoff flange in which the hollow piston is secured and which is located in the upper housing part, the locking mechanism according to the invention situated in the upper housing part, a spring housing with the spring contained therein, which is rotatably mounted on the upper housing part by means of a rotary bearing, a lower housing part which is fitted onto the spring housing in the axial direction, and an adapter in the form of a hollow cavity with two opposite openings, the smaller opening fitting closely around at least the point of exit of the aerosol from the nozzle, and the larger opening having a contour which makes it possible to fit this opening over an eye.

The hollow piston with valve body corresponds to a device disclosed in WO 97/12687. It projects partially into the cylinder of the pump housing and is axially movable within the cylinder. Reference is made in particular to FIGS. 1 to 4, especially FIG. 3, and the relevant parts of the description. The hollow piston with valve body exerts a pressure of 5 to 60 Mpa (about 50 to 600 bar), preferably 10 to 60 Mpa (about 100 to 600 bar) on the fluid, the measured amount of active substance solution, at its high pressure end at the moment when the spring is actuated. Volumes of 10 to 50 microliters are preferred, while volumes of 5 to 20 microliters are particularly preferred and a volume of 15 microliters per spray is most particularly preferred.

The valve body is preferably mounted at the end of the hollow piston facing the valve body.

The nozzle in the nozzle body is preferably microstructured, i.e. produced by microtechnology. Microstructured nozzle bodies are disclosed for example in WO-94/07607; reference is hereby made to the contents of this specification, particularly FIG. 1 therein and the associated description.

The valve body consists for example of two sheets of glass and/or silicon firmly joined together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns while the length is preferably 7 to 9 microns.

In the case of a plurality of nozzle openings, preferably two, the directions of spraying of the nozzles in the nozzle body may extend parallel to one another or may be inclined relative to one another in the direction of the nozzle opening. In a nozzle body with at least two nozzle openings at the outlet end the directions of spraying may be at an angle of 20 to 160° to one another, preferably 60 to 150°, most preferably 80 to 100°. The nozzle openings are preferably arranged at a spacing of 10 to 200 microns, more preferably at a spacing of 10 to 100 microns, most preferably 20 to 50 microns. Spacings of 22 to 28 microns are most preferred. The jets will therefore meet right in front of the nozzle openings.

As already mentioned, the liquid pharmaceutical preparation is under an entry pressure of up to 600 bar, preferably 200 to 300 bar, at the entrance to the nozzle body and is atomised into an inhalable aerosol through the nozzle openings. The preferred particle sizes of the aerosol are up to 20 microns, preferably 3 to 10 microns.

The lower housing part is pushed axially over the spring housing and covers the mounting, the drive of the spindle and the storage container for the fluid.

When the atomiser is actuated the upper housing part is rotated relative to the lower housing part, the lower housing part taking the spring housing with it. The spring is thereby compressed and biased by means of the helical thrust gear and the locking mechanism engages automatically. The angle of rotation is preferably a whole-number fraction of 360 degrees, e.g., 180 degrees. At the same time as the spring is biased, the power takeoff part in the upper housing part is moved along by a given distance, the hollow piston is withdrawn inside the cylinder in the pump housing, as a result of which some of the fluid is sucked out of the storage container and into the high pressure chamber in front of the nozzle.

If desired, a number of exchangeable storage containers which contain the fluid to be atomised may be pushed into the atomiser one after another and used in succession. The storage container contains the aqueous aerosol preparation according to the invention.

The atomising process is initiated by pressing gently on the actuating button. As a result, the locking mechanism opens up the path for the power takeoff member. The biased spring pushes the piston into the cylinder of the pump housing. The fluid leaves the nozzle of the atomiser in atomised form.

If desired, some of the elements of the nebuliser that come into contact with the liquid being administered as it travels from the storage container to the nozzle may be made of oligodynamically active ingredients or be coated with germicidal materials. Alternatively, or in addition, a germ-repellent filter may be formed in this pathway. Such embodiments have the advantage that no pathogens can get into the storage container from outside and therefore there is no need to add any preservatives. This is particularly advantageous for long-term use, as explained hereinbefore.

Further details of construction are disclosed in PCT Applications WO 97/12687 and WO 97/20590, to which reference is hereby made once more.

The components of the atomiser (nebuliser) are made of a material which is suitable for its purpose. The housing of the atomiser and, if its operation permits, other parts as well are preferably made of plastics, e.g., by injection moulding. For medicinal purposes, physiologically safe materials are used.

FIGURES

The invention is explained more fully by means of the drawings. FIG. 1*a* and FIG. 1*b* show a longitudinal section through a locking tensioning mechanism according to the prior art, i.e. without an additional component according to the invention. The upper cylindrical housing part (1) engages over the spring housing (2), to which it is connected by means of snap-in lugs (3). The snap-in lugs (3) are provided on the outside of the spring housing (2) and may extend over two opposing segments of a circle, each measuring 30 degrees. They engage in an encircling groove on the inside of the upper housing part (1). The two housing parts are also rotatable relative to one another. In the spring housing is the compression spring (4), which is generally already pretensioned when the two housing parts are put together. The compression spring (4) is supported on an encircling projection on the lower end of the spring housing as well as on the spring component (5), which is mounted so as to be paraxially movable between the upper housing part and the spring housing, and which in turn bears on the upper housing part (1). The cup-shaped spring component (5) projects into the upper housing part (1). The annular locking member (6) surrounds the spring component. The actuating button (7) provided on the locking member projects laterally from the upper housing part. The collar of the cup-shaped spring component is provided, e.g., on its inside with two saw-tooth-shaped recesses over which two saw teeth in the upper housing part slide. The saw teeth and the recesses are shown in highly simplified form in FIG. 1*a*. When the upper housing part is rotated counter to the spring housing the axially movable spring component is pressed further into the spring housing counter to the force of the compression spring. As soon as the upper edge of the cup-shaped spring component has been pressed sufficiently far down by the locking member, the annular locking member moves perpendicular to the housing axis (dotted line in the drawings) between the upper edge of the cup-shaped spring component and an annular projection in the upper housing part and secures the spring component and the compression spring which has been (additionally) biased by the movement of the spring component in the position reached.

By pressing the actuating button (7) the annular locking member (6) is pushed back perpendicular to the housing axis, thereby freeing the spring component to move. The compression spring pushes the spring component upwards over a given distance by means of the annular locking member and thereby actuates a component connected to the spring component, but not shown in FIG. 1*a* and FIG. 1*b*, e.g., it moves a piston in a cylinder.

In FIG. 1*a* the locking tensioning mechanism with the spring component is shown in its second resting position and with the locking member disengaged. FIG. 1*b* shows the locking tensioning mechanism with the spring component in its first resting position and the locking member engaged. The first stop (8) is the travel limiter for the spring component in its first resting position, the second stop (9) is the travel limiter for the spring component in its second resting position. By rotating the two housing parts relative to one another the state shown in FIG. 1*a* changes into the state shown in FIG. 1*b*. After the actuating button has been pressed the force of the tensioned compression spring changes the state according to FIG. 1*b* into the state according to FIG. 1*a*. In FIGS. 1*a* and 1*b* the distance (a) is the distance travelled by the spring component.

FIGS. 2 to 7 show various locking tensioning mechanisms according to the invention, in which the travel of the spring component is variable.

FIG. 2 shows the spring component (5) in its second resting position, while the spring component bears on the second stop (9). In addition to the components described, the flat ring (10) is disposed on the bottom of the cup-shaped spring component (5). This ring is placed in the spring component during the assembly of the locking tensioning mechanism. The travel (b) of the spring component is altered by an amount equal to the thickness of the flat ring (10). The ring (10) alters the quantity of liquid which can be expelled by a piston (not shown) connected to the spring component (5).

FIG. 3 also shows the spring component (5) in its second resting position, while the spring component bears on the second stop (9). On the bottom of the cup-shaped spring component is a two-part stepped disc (11*a*; 11*b*), which is placed in the spring component during the assembly of the locking tensioning mechanism. Each of the two discs (11*a*) and (11*b*) comprises a plurality of steps, e.g., four steps, on the sides facing one another, each step being provided several times, e.g., three times, on each disc. The four steps of equal height are each offset from one another by an angle of 120 degrees. If the highest step on one disc is located on the lowest step of the other disc, the two-part stepped disc is at its minimum thickness. If the highest step on one disc is located on the highest step of the other disc, the two-part stepped disc is at its maximum thickness. The travel (c) of the spring component is altered by an amount corresponding to the thickness of the two-part stepped disc (11a; 11b).

FIGS. 4a and 4b show the spring component (5) in its second resting position, while the spring component bears on the second stop (9). A plurality of adjustment screws are screwed into the upper housing part (1), which are offset from one another by 120 degrees, for example, in the case of three screws. FIGS. 4a and 4b show only one of these screws in each case. The adjustment screws (12) are also accessible from outside after the assembly of the locking tensioning mechanism. All the adjustment screws (12) on a locking tensioning mechanism are screwed in to the same depth, but the specified depth of penetration may be different within the adjustment area and may be varied continuously. The ends of the adjustment screws within the upper housing part (1) determine the second stop (9) for the spring component. In FIG. 4a the adjustment screws (12) are screwed in less deeply than in FIG. 4b. The travel (d1) of the spring component in FIG. 4a is longer than the travel (d2) of the spring component in FIG. 4b.

Figure 5B:
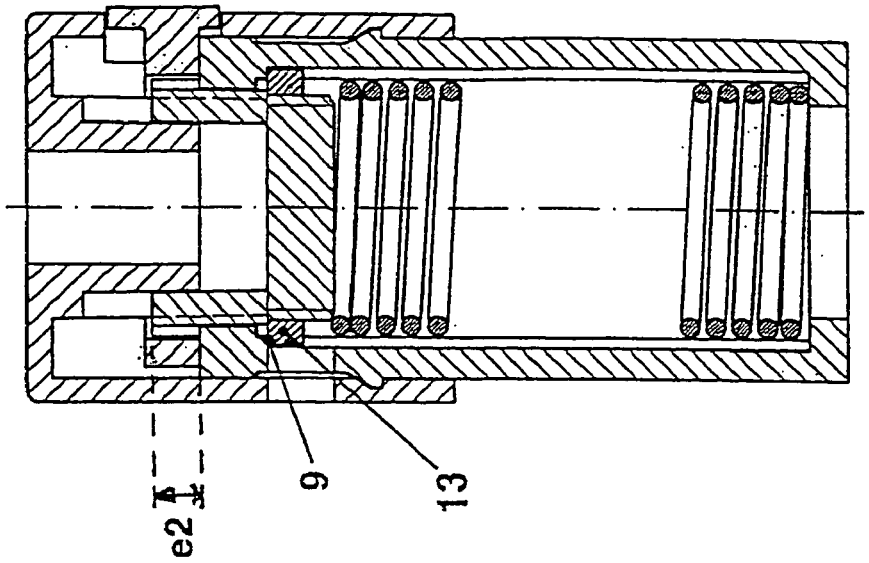
Figure 5A:
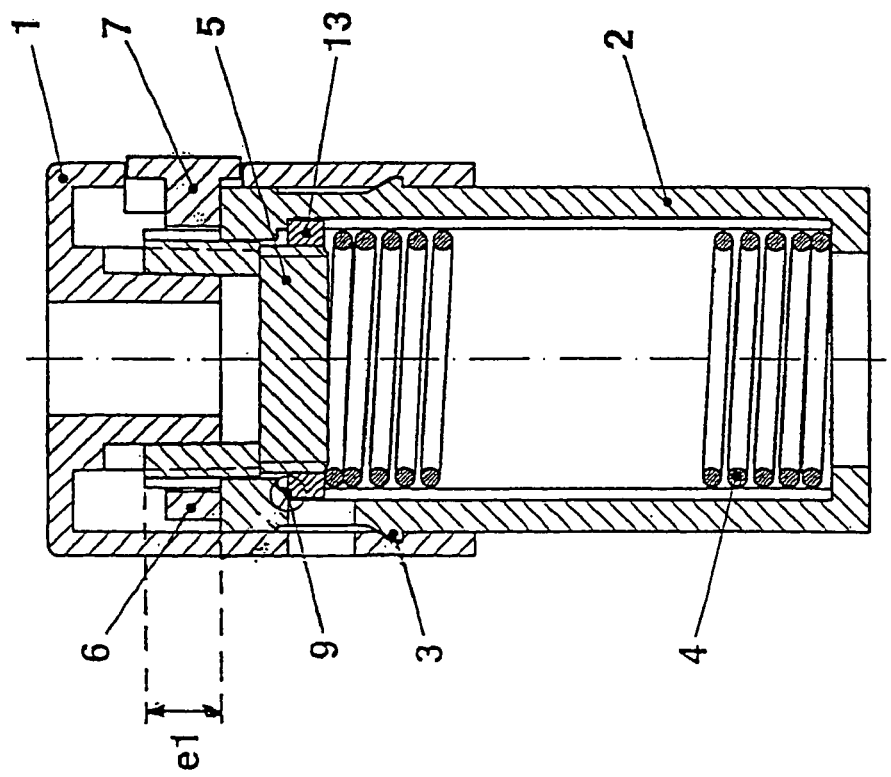

FIGS. 5a and 5b show the spring component (5) in its second resting position. The spring component is provided, at its end facing the spring (4), with a locknut (13) which can be turned by different amounts onto the spring component. In the second resting position of the spring component the top of the locknut (13) bears on the stop (9). The further the locknut (13) is screwed onto the spring component, the shorter the travel of the spring component. The travel (e2) is shorter than the travel (e1).

Figure 2:
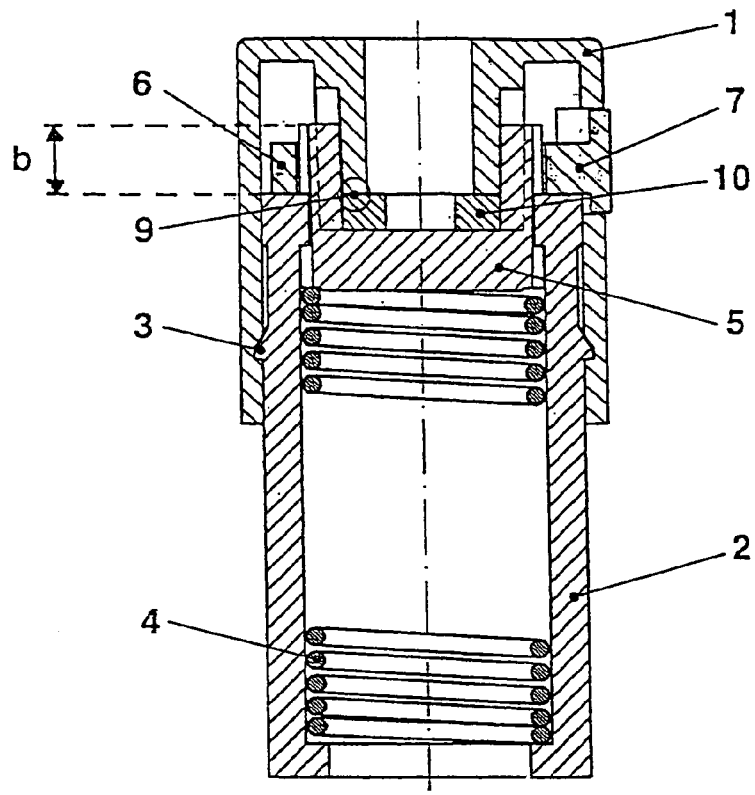
Figure 3:
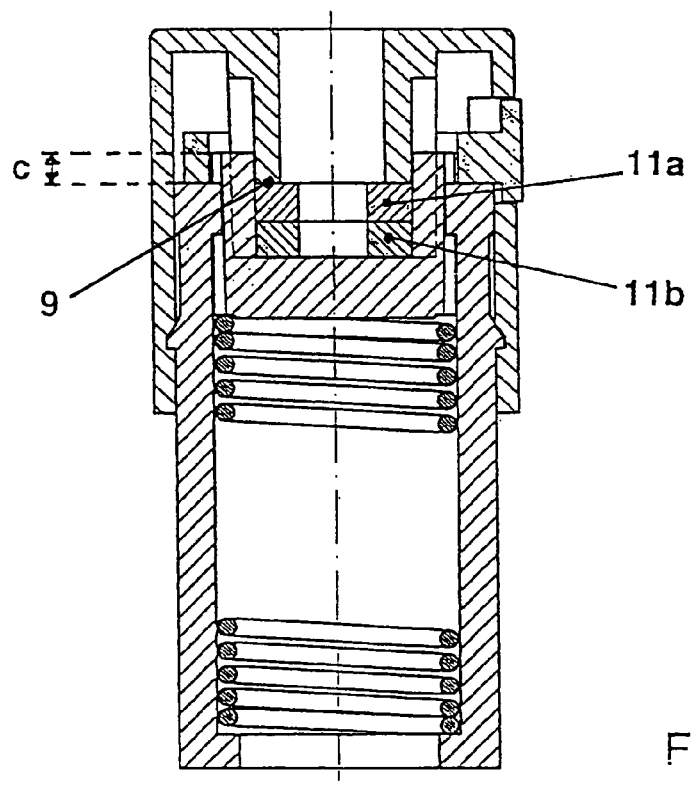

FIGS. 6a and 6b show, apart from the locking tensioning mechanism, a cylinder (21) which is fixed in the upper housing part (1), and a hollow piston (22) which is fixed in the spring component (5). At the end of the cylinder is the nozzle (23). The travel of the hollow piston is also exactly the same length as the travel of the spring component. On the base of the cup-shaped spring component is a plate (24), the spacing of which from the bottom of the cup-shaped spring component is continuously variable by means of adjustment screws (25). The adjustment screws (25) are accessible from outside after the assembly of the locking tensioning mechanism. The further the plate (24) is from the bottom of the cup-shaped spring component, the shorter the travel of the spring component. The travel (f2) is shorter than the travel (f1). FIGS. 6a and 6b are similar in their content to FIGS. 6a and 6b of WO 97/12687, which show a nebuliser which is preferably used as an inhaler. Reference is specifically made to these Figures and the associated remarks within the scope of the present invention. Reference is also made to FIGS. 1 and 2 of WO 01/64268, which show a needleless injector and to FIGS. 4 and 5 of PCT/EP0207038, which illustrate an apparatus for producing an eye spray.

Figure 7B:
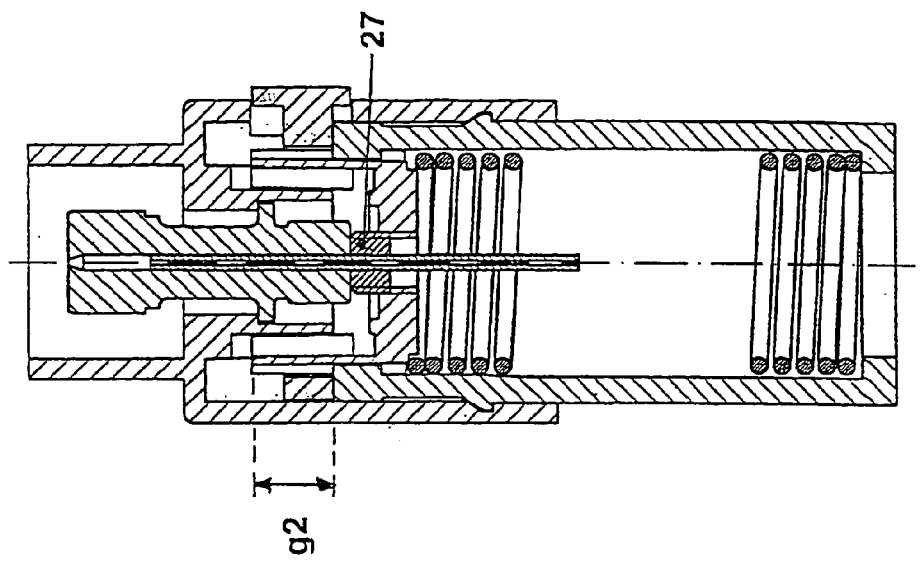
Figure 7A:
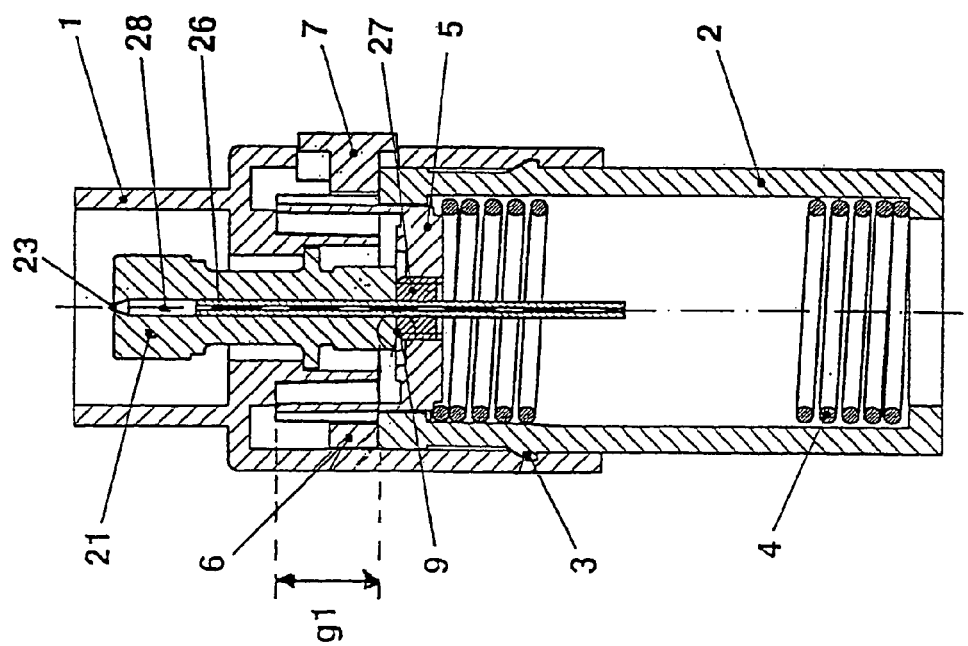

FIGS. 7a and 7b show a locking tensioning mechanism, a cylinder (21) secured in the upper housing part (1) and a hollow piston (26). The hollow piston is fixed in the central adjusting screw (27) which can be screwed to different depths into the bottom of the cup-shaped spring component. The central adjusting screw (27) is accessible from the outside after the assembly of the locking tensioning mechanism. The more deeply the central adjusting screw is screwed into the bottom of the cup-shaped spring component, the shorter the travel of the spring component and hence the travel of the hollow piston within the cylinder. In this arrangement of the hollow piston the clearance volume (28) between the nozzle and the nozzle end of the hollow piston remains unchanged when the central adjusting screw is screwed to different depths into the bottom of the spring component. The travel (g2) is shorter than the travel (g1).

FIGS. 8 to 14 show details of a helical thrust gear for setting a stop of the spring component.

FIG. 8 shows the rotatable adjusting ring (32) and the axially movable ring (36) in exploded view. The rotatable adjusting ring (32) shown in FIG. 8a is located within the housing (31) (shown only in part). The handle (33) of the rotatable adjusting ring is accessible from the outside and can be moved within a slot in the housing. On one edge of the rotatable adjusting ring there are engaging teeth (35) which cooperate with engaging teeth (not shown) in the housing. The other edge of the rotatable adjusting ring is a double-threaded helicoidal surface (34a; 34b). Each of the two screw threads extends over an angle of 180 degrees.

The slidable ring (36) shown in FIG. 8b also has a double-threaded helicoidal surface (37a; 37b) on the edge facing the rotatable adjusting ring (32). Each of the two screw threads extends over an angle of 180 degrees. The double-threaded helicoidal surface of the axially movable rings has the same thread height as the double-threaded helicoidal surface of the rotatable adjusting ring.

The axially movable ring is prevented from rotating by means of guide bars (38). The guide bars slide in grooves (not shown) in the housing.

The helicoidal surface of the axially movable ring (36) is pressed against the helicoidal surface of the rotatable adjusting ring by the resetting spring (39). The helical spring is shown in cross section. As the rotatable adjusting ring is rotated, the helicoidal surface (34a) slides over the helicoidal surface (37a) and the helicoidal surface (34b) slides over the helicoidal surface (37b).

The smooth edge (40) of the axially movable ring (36) is the abutment for the spring component (not shown) of the locking tensioning mechanism.

FIG. 9 shows another embodiment of a helical thrust gear for setting a stop of the spring component. FIG. 9a corresponds to FIG. 8a. Of the helicoidal surface (37a; projections are retained in FIG. 9b. The remaining areas of the helicoidal surface 37b) in FIG. 8b, only the end surfaces (41a; 41b) and (42a; 42b) on the four (37a; 37b) are cut away. The helical spring (40) (shown in cross section) presses the end surfaces (41a; 41b) against the helicoidal surface (34a) and the end surfaces (42a; 42b) against the helicoidal surface (34b) of the rotatable adjusting ring.

The azimuthal spacings between the projections, for example four projections, may be 90 degrees in each case. The azimuthal spacings may optionally be of different sizes. The free spaces between the projections may be used for other purposes, for example for construction elements provided between the housing wall and the inner region of the two rings.

Figures 10, 10A, 10B:
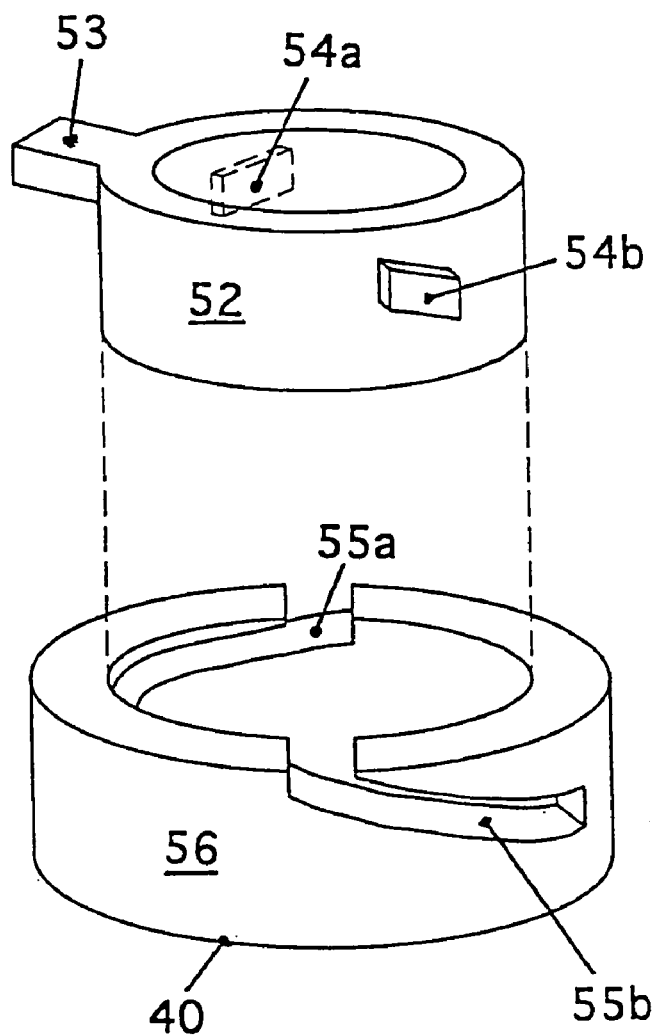

FIGS. 10a and 10b show another embodiment of a helical thrust gear for setting a stop of the spring component. In this Example the rotatable adjusting ring (52) has two cams on its outer wall (54a; 54b). The axially movable ring (56) has two detents (55a; 55b), which are parts of a double-threaded helicoidal surface. The external diameter of the rotatable adjusting ring (52) is almost as great as the internal diameter of the axially movable ring (56). When the two rings are fitted into one another the two cams (54a; 54b) engage in the detents (55a; 55b). When the rotatable adjusting ring (52) is rotated counter to the axially movable ring (56) the cams slide in the detents. The cams move the ring (56) axially in each direction of rotation of the rotatable adjusting ring. There is no need for a resetting spring for the axially movable ring in this embodiment.

The cams or the detents, respectively, may be associated with the two rings in a different manner. For example, the cams may be provided on the inner wall of the axially movable ring and the detents in the wall of the rotatable adjusting ring. It may be expedient to make the radial depth of the detents smaller than the radial thickness of the ring provided with detents.

The cams shown in FIG. 10a have a shape resembling a helicoidal surface. Their height in the axial direction substantially corresponds to the height of the detents in the axial direction. Instead of cams of this kind, cylindrical cams may be used, for example, the diameter of which is substantially as great as the height of the detents in the axial direction.

FIGS. 11a and 11b shows another embodiment of a rotatable adjusting ring (62) and an axially movable ring (66) in diagonal view. Both rings have a quadruple-threaded helicoidal surface, each provided with two engaging steps. The helicoidal surfaces (64a; 64d) on the rotatable adjusting ring are visible in FIG. 11a; the other two helicoidal surfaces on the rotatable adjusting ring are hidden in FIG. 11a. The axially movable ring (66) has the four corresponding helicoidal surfaces (67a; 67b; 67c; 67d), which cooperate with the associated helicoidal surfaces on the rotatable adjusting ring.

Each of the four helicoidal surfaces on each of the two rings merges into two engaging steps, of which the four "high" steps in each case are in one plane and the four "low" steps are in a plane parallel thereto. The two planes are perpendicular to the axis of the rotatable adjusting ring. The "high" steps on the rotatable adjusting ring extend in each case over an angle which is essentially exactly the same size as the angle over which the "low" steps on the axially movable ring extend. The "low" steps on the rotatable adjusting ring extend in each case over an angle over which the "high" steps on the axially movable ring extend.

The "high" steps on the rotatable adjusting ring may in each case be provided with a recess, of which only the recess (65a) is visible in one of these four steps in FIG. 11a; the recesses in the other "high" steps of the rotatable adjusting ring are hidden in FIG. 11a. The recesses in the "high" steps of the rotatable adjusting ring extend in each case over an angle which is substantially equal to the angle over which the "high" steps of the axially movable ring extend.

FIG. 12 shows the two rings of the helical thrust gear for setting a stop of the spring component of the locking tensioning mechanism in the position in which the "high" steps of one ring are located in the "low" steps of the other ring. FIG. 12a shows this arrangement in diagonal view and FIG. 12b shows a longitudinal section through the axis of the rings. FIG. 12b shows the recess (65c), which is now visible.

In FIG. 13 the two rings of the helical thrust gear for setting a stop of the spring component of the locking tensioning mechanism are shown in the position in which the "high" steps of both rings are located one above the other. FIG. 13a shows the arrangement viewed diagonally and FIG. 13b shows a longitudinal section through the axis of the two rings.

FIG. 13a shows the two recesses (65a; 65d), while FIG. 13b shows the recesses (65b; 65c) which are now visible.

FIG. 14 shows the arrangement of the helical thrust gear for setting a stop of the spring component within the housing in longitudinal section through the axis of the housing, which coincides with the axis of the two rings. FIG. 14a shows the position of the two rings corresponding to FIG. 12 and FIG. 14b shows those corresponding to FIG. 13. In FIGS. 14a and 14b the thread height of the helicoidal surfaces is shown exaggeratedly large.

The housing (31) contains the operating spring (4), one end of which abuts on the spring component (5). The spring component bears on the stop (40) on one side of the axially movable ring (66). The quadruple-threaded helicoidal surface of the axially movable ring cooperates with the helicoidal surface of the rotatable ring (62). The axially movable ring (66) is prevented from rotating by means of the guide bars (38), which slide in guide grooves in the wall of the housing. The resetting spring (39) holds the axially movable ring in contact with the rotatable adjusting ring.

FIG. 14c shows a cross section through the arrangement according to FIG. 14a level with the plane A-A.

In the embodiment of the invention according to FIGS. 11 to 14 the rotatable adjusting ring can be rotated through 90 degrees between the two positions of engagement. The axially movable ring (66) then moves, taking with it one stop of the spring component (5), by a distance (X), which is shown between the two Figures.

Within the scope of the invention there are other possible ways of varying the travel of the spring component. It may be expedient to divide the travel of the spring component into a number of parts which are covered one after another. This makes it possible, for example, with a needleless injector, to deliver the quantity of liquid corresponding to the travel of the spring component laid down by the helical thrust gear for the purpose of tensioning the operating spring on the transition from the second resting position into the first resting position, in a plurality of partial amounts, without re-activating the locking tensioning mechanism of the needleless injector all the time.

What is claimed is:

1. Locking tensioning mechanism for a miniaturised high pressure generator, comprising:
    two housing parts mounted to be rotationally movable relative to one another,
    an operating spring that acts as a store for the mechanical energy acting on a spring component,
    a device for tensioning the operating spring,
    a first and a second stop for the spring component,
    a piston connected to the spring component that is moved in an axial direction in a cylinder as the spring component moves, and
    a nozzle at the end of the cylinder through which the volume of liquid is expelled by the piston, and
    a central securing the piston to the spring component, the central screw having an inner end projecting into the spring component operating to alter and determine the position of the second stop of the spring component.

* * * * *